(12) United States Patent
Wei et al.

(10) Patent No.: US 11,604,128 B1
(45) Date of Patent: Mar. 14, 2023

(54) SELF DRILLING PRESSURE SIMULATION TEST DEVICE AND METHOD FOR FORMATION CONTAINING NATURAL GAS HYDRATE

(71) Applicant: INSTITUTE OF ROCK AND SOIL MECHANICS, CHINESE ACADEMY OF SCIENCES, Wuhan (CN)

(72) Inventors: Houzhen Wei, Wuhan (CN); Hao Liu, Wuhan (CN); Qiang Xue, Wuhan (CN); Qingshan Meng, Wuhan (CN); Xiaoxiao Li, Wuhan (CN); Rui Xu, Wuhan (CN)

(73) Assignee: INSTITUTE OF ROCK AND SOIL MECHANICS, CHINESE ACADEMY OF SCIENCES, Wuhan (CN)

( * ) Notice: Subject to any disclaimer, the term of this patent is extended or adjusted under 35 U.S.C. 154(b) by 0 days.

(21) Appl. No.: 17/653,841

(22) Filed: Mar. 7, 2022

(30) Foreign Application Priority Data

Sep. 26, 2021 (CN) .......................... 202111128123.X

(51) Int. Cl.
*G01N 3/56* (2006.01)
*G01N 3/04* (2006.01)
(Continued)

(52) U.S. Cl.
CPC ................. *G01N 3/56* (2013.01); *G01N 3/04* (2013.01); *G01N 33/24* (2013.01); *E21B 41/0099* (2020.05)

(58) Field of Classification Search
CPC ...... E21B 43/24; E21B 43/34; E21B 41/0099; G06F 2111/10; G01N 3/56; G01N 3/04;
(Continued)

(56) References Cited

U.S. PATENT DOCUMENTS

2016/0357888 A1* 12/2016 Li .............................. E21B 7/00
2018/0172574 A1*  6/2018 Li .............................. B01J 3/03
2020/0232305 A1*  7/2020 Chen ....................... E21B 43/36

FOREIGN PATENT DOCUMENTS

CN          102252918 A     11/2011
CN          102926369 A      2/2013
(Continued)

*Primary Examiner* — Brandi N Hopkins
(74) *Attorney, Agent, or Firm* — Platinum Intellectual Property PC

(57) ABSTRACT

The invention provides a self drilling side pressure simulation test device and method for a formation containing natural gas hydrate, belonging to the technical field of geotechnical mechanics. The device comprises a reactor, a cutting tool, a mud conveying mechanism and a side pressure testing device. The reactor is used to fill the simulated substance of the formation containing natural gas hydrate to be tested. The cutting tool is arranged in the reactor, and the cutting tool can move up and down relative to the reactor. One end of the mud conveying mechanism is connected with the reactor, for outputting the mud cut by the cutting tool from the reactor; The side pressure test device can complete the side pressure test experiment with the cutting tool moving to the set depth. The method is implemented based on the device. The in-situ test method can directly test the engineering mechanical parameters of the formation containing natural gas hydrate. At the same time, it is of great significance to the formation stability of natural gas hydrate development and the prevention and control of engineering disasters.

8 Claims, 5 Drawing Sheets

(51) Int. Cl.
*E21B 41/00* (2006.01)
*G01N 33/24* (2006.01)

(58) Field of Classification Search
CPC .......... G01N 33/24; G01N 7/00; G01N 3/567; G01N 33/222; G01N 27/041; G01N 5/04; G01D 21/02
See application file for complete search history.

(56) References Cited

FOREIGN PATENT DOCUMENTS

| | | |
|---|---|---|
| CN | 108445189 A | 8/2018 |
| CN | 210815185 U | 6/2020 |
| CN | 211098930 U | 7/2020 |

* cited by examiner

SELF DRILLING PRESSURE SIMULATION TEST DEVICE AND METHOD FOR FORMATION CONTAINING NATURAL GAS HYDRATE

RELATED APPLICATIONS

This application is a Non-provisional Application under 35 USC § 111(a), which claims priority to Chinese Patent Application Serial No. 202111128123.X, filed Sep. 26, 2021, the disclosure of all of which is hereby incorporated by reference in its entirety.

TECHNICAL FIELD

The invention relates to the technical field of geotechnical mechanics, in particular to a self drilling side pressure simulation test device and method for formation containing natural gas hydrate.

BACKGROUND TECHNOLOGY

Natural gas hydrate is usually distributed in the deep-sea shallow sediments of permafrost areas or continental margins. Under certain temperature and pressure conditions, methane gas and water combine to form cage compounds. In recent 20 years, although scholars at home and abroad have done a lot of research on sediments containing natural gas hydrate, in terms of submarine hydrate reservoir, because natural gas hydrate is in deep-sea environment, it is sensitive to the changes of storage environment temperature and pressure, it is easy to decompose, it is difficult to obtain its original sample, and the test of key physical and mechanical parameters is inaccurate.

SUMMARY OF THE INVENTION

In view of this, the invention provides a self drilling side pressure simulation test device and method for the formation containing natural gas hydrate. The in-situ test method can directly test the engineering mechanical parameters of the formation containing natural gas hydrate. At the same time, it is of great significance to the formation stability of natural gas hydrate development and the prevention and control of engineering disasters, so it is more suitable for practical use.

In order to achieve the above first purpose, the technical scheme of the self drilling pressure simulation test device for formation containing natural gas hydrate provided by the invention is as follows:

The self drilling side pressure simulation test device for formation containing natural gas hydrate provided by the invention comprises a reactor (1), a cutting tool, a mud conveying mechanism and a side pressure test device (14), The reactor (1) is used to fill the simulated substance of the formation containing natural gas hydrate to be tested, The cutting tool is arranged in the reactor (1), and the cutting tool can move up and down relative to the reactor (1), One end of the mud conveying mechanism is connected with the reactor (1) for outputting the mud cut by the cutting tool from the reactor (1);

The side pressure test device (14) can complete the side pressure test experiment with the cutting tool moving to a set depth.

The self drilling side pressure simulation test device for formation containing natural gas hydrate provided by the invention can also be further realized by adopting the following technical measures.

Preferably, the reactor (1) is provided with an air inlet and outlet (7).

Preferably, the test gas hydrate containing formation simulation material includes saturated sediments and methane gas.

Preferably, the reactor (1) comprises a reactor inner tank (2), a reactor filter screen (4), a lifting rod (17), The filter screen (4) is arranged on the top of the reaction kettle (2), The lifting rod (17) can move up and down relative to the reactor filter screen (4), The cutting tool is fixedly connected to the bottom of the lifting rod (17).

Preferably, the mud conveying mechanism comprises a screw conveyor (34).

Preferably, the cutting tool comprises a cutting cutter head (25), a side wall and a sludge storage bin partition (31), The sludge storage bin (30) is enclosed between the cutting cutter head (25), the side wall and the sludge storage bin partition (31), The cutting tool (25) is provided with a hollow out, Through the hollowing out, the mud cut by the cutting tool (25) can enter the mud storage bin (30), The screw conveyor (34) is communicated with the sludge storage bin (30) through one end thereof.

Preferably, the cutting tool further comprises a balance chamber diaphragm (33), a transmission bearing platform (28), The balance bin partition (33), the sludge bin partition (31) and the side wall are enclosed to obtain a pneumatic balance bin (32), The driving bearing platform (28) is pressed above the diaphragm (31) of the sludge storage bin.

Preferably, the reactor (1) further comprises a reactor shell (3) and a cooling pipe, A holding space is arranged between the inner tank (2) of the reactor and the shell (3) of the reactor, The cooling pipe is arranged in the holding space.

Preferably, the self drilling pressure meter simulation test device for gas hydrate bearing formation further comprises an insulating layer (6), The insulating layer (6) is arranged in the holding space.

Preferably, the self drilling pressure simulation test device for gas hydrate containing formation further comprises a reactor sealing cover (5), The reactor sealing cover (5) is arranged above the reactor inner tank (2), so that the reactor inner tank (2) forms a closed space.

Preferably, the self drilling pressure meter simulation test device for the formation containing natural gas hydrate also includes a temporary soil storage bin (16), which is arranged in the sealing cover (5) of the reactor, The other end of the mud conveying mechanism is connected with the temporary soil storage bin (16).

Preferably, the self drilling pressure simulation test device for gas hydrate containing formation further comprises an electromagnetic sealing gasket (9), The electromagnetic sealing gasket (9) is arranged between the reactor sealing cover (5) and the reactor (1).

Preferably, the self drilling type pressure meter simulation test device for the formation containing natural gas hydrate also comprises a frame and a pair of overturning supports (19), The outer side of the turnover bracket (19) is arranged on the frame, the setting height of the pair of turnover brackets (19) is the same, and the turnover bracket (19) can rotate relative to the frame;

The inner side of the turnover support (19) is fixedly connected to the reactor (1).

As a preferred method, the self drilling bypass pressure simulation test device for formation containing natural gas hydrate also includes a pair of lifting supports (20), lifting transmission chain (21) and lifting motor (22), The inner side of the liftable support (20) is fixedly connected to the reactor sealing cover (5), The outer side of the lifting support (20) is connected to the lifting transmission chain (21), The lifting motor (22) controls the lifting of the liftable support (20) by controlling the lifting transmission chain (21).

Preferably, the self drilling pressure simulation test device for formation containing natural gas hydrate also comprises a differential transformer (11), a signal amplifier, a signal control positioner, a hydraulic regulating valve (10), a proportional flow valve (12) and a pressure sensor (13), The hydraulic regulating valve (10) and the proportional flow valve (12) are arranged on the sealing cover (5) of the reactor, wherein the hydraulic regulating valve (10) is used to regulate the gas flow entering the reactor (1), and the proportional flow valve (12) is used to regulate the gas flow discharged from the reactor (1), The pressure sensor (13) is used to obtain the pressure data in the reactor (1);

The differential transformer (11) is used to convert the pressure signal obtained from the pressure sensor into an electrical signal, amplify the electrical signal through the signal amplifier and transmit it to the signal control positioner, so as to control the opening of the hydraulic regulating valve (10).

Preferably, the self drilling type pressure meter simulation test device for gas hydrate bearing formation also comprises a spiral drive probe rod (17) and a drilling motor (18), The drilling motor (18) is used to control the movement of the spiral drive probe rod (17) in the vertical direction.

Preferably, the self drilling pressure simulation test device for gas hydrate containing formation also includes a measuring chamber, and the side wall of the measuring chamber is provided with an elastic film (42).

Preferably, the self drilling pressure simulation test device for gas hydrate containing formation is characterized in that it also includes a main cutter (39), a leading cutter (40) and a scraper (41), The main cutter (39), the leading cutter (40) and the scraper (41) are arranged inside the cutting cutter head (25).

In order to achieve the above second purpose, the technical scheme of the self drilling bypass pressure simulation test method for formation containing natural gas hydrate provided by the invention is as follows:

The self drilling side pressure simulation test method of the formation containing natural gas hydrate provided by the invention is realized based on the self drilling side pressure simulation test device of the formation containing natural gas hydrate provided by the invention. The self drilling side pressure simulation test method of the formation containing natural gas hydrate comprises the following steps:

Filling the simulated substance of the formation containing natural gas hydrate to be tested into the reactor (1);

Introducing methane with a set temperature into the reactor (1) to form a simulated test environment in the reactor (1);

Causing the cutting tool to perform a cutting action on the simulated substance of the formation containing natural gas hydrate to be tested;

Starting the mud conveying mechanism so that the cutting tool and the obtained mud are output from the reactor (1);

In the process of performing the cutting action of the simulated material of the natural gas hydrate containing formation to be tested, the side pressure test device (14) performs and completes the self drilling side pressure simulation test experiment of the natural gas hydrate containing formation.

The self drilling bypass pressure simulation test method for the formation containing natural gas hydrate provided by the invention can also be further realized by the following technical measures.

Preferably, the self drilling bypass pressure simulation test method for formation containing natural gas hydrate also includes the following steps:

Make the cutting tool perform the action of continuing drilling downward until the cutting tool reaches the next set depth, and complete the side pressure test experiment of the simulated substance of the formation containing natural gas hydrate to be tested at the next depth.

Through the test data obtained by the self drilling pressure meter simulation test device and method for formation containing natural gas hydrate provided by the invention, the self drilling pressure meter test can obtain the following results: determine the mechanical parameters such as foundation bearing capacity, soil shear modulus, pore water pressure, in-situ lateral pressure, static lateral stress coefficient, pore wall displacement, undrained shear strength, etc., The shrinkage and expansion of cylindrical cavity can also be analyzed by the obtained loading curve.

DESCRIPTION OF ATTACHED DRAWINGS

By reading the detailed description of the preferred embodiments below, various other advantages and benefits will become clear to those skilled in the art. The drawings are only for the purpose of showing the preferred embodiment and are not considered to be a limitation of the present invention. Moreover, throughout the drawings, the same components are represented by the same reference symbols. In the attached drawings.

DESCRIPTION OF REFERENCE MARKS

1—reactor, 2—reactor liner, 3—reactor shell, 4—reactor filter screen, 5—reactor sealing cover, 6—reactor insulation layer, 7—inlet and outlet, 8—sealing buckle, 9—electromagnetic sealing gasket, 10—hydraulic regulating valve, 11—differential transformer, 12—proportional flow valve, 13—pressure sensor, 14 side pressure test device, 15 screw transmission motor, 16 temporary soil storage bin, 17—screw drive probe rod, 18—drilling motor, 19—turnover support, 20—lifting support, 21—lifting transmission chain, 22—lifting motor, 23—cable and impulse pipe inlet, 24—hydraulic jack, 25—cutting cutter head, 26—cutter head support frame, 27—bearing, 28—transmission bearing platform, 29—hydraulic Marta, 30—sludge storage bin, 31—partition board of sludge storage bin, 32—pneumatic balance bin, 33—partition board of balance bin, 34—screw conveyor, 35—screw center rod, 36—multi-core cable, 37—infusion pipe, 38—impulse pipe, 39—main cutter, 40—advance cutter, 41—scraper, 42—elastic film, 43—protective armor, 44—displacement sensor.

Specific Implementation Mode

In view of this, the invention provides a self drilling side pressure simulation test device and method for the formation containing natural gas hydrate. The in-situ test method can directly test the engineering mechanical parameters of the formation containing natural gas hydrate. At the same time, it is of great significance to the formation stability of natural gas hydrate development and the prevention and control of engineering disasters, so it is more suitable for practical use.

In order to further elaborate the technical means and efficacy adopted by the invention to achieve the intended purpose of the invention, the following is a detailed description of the specific implementation formula, structure, characteristics and efficacy of a self drilling side pressure simulation test device and method for formation containing natural gas hydrate proposed according to the invention in combination with the attached drawings and preferred embodiments. In the following description, different "one embodiment" or "embodiment" do not necessarily refer to the same embodiment. Further, specific features, structures, or features in one or more embodiments may be combined in any suitable form.

The term "and/or" in this paper is only an association relationship describing the association object, which means that there can be three kinds of relationships, for example, a and/or B. specifically, it can include both a and B, a alone or B alone, which can meet any of the above three situations.

Figure 1:
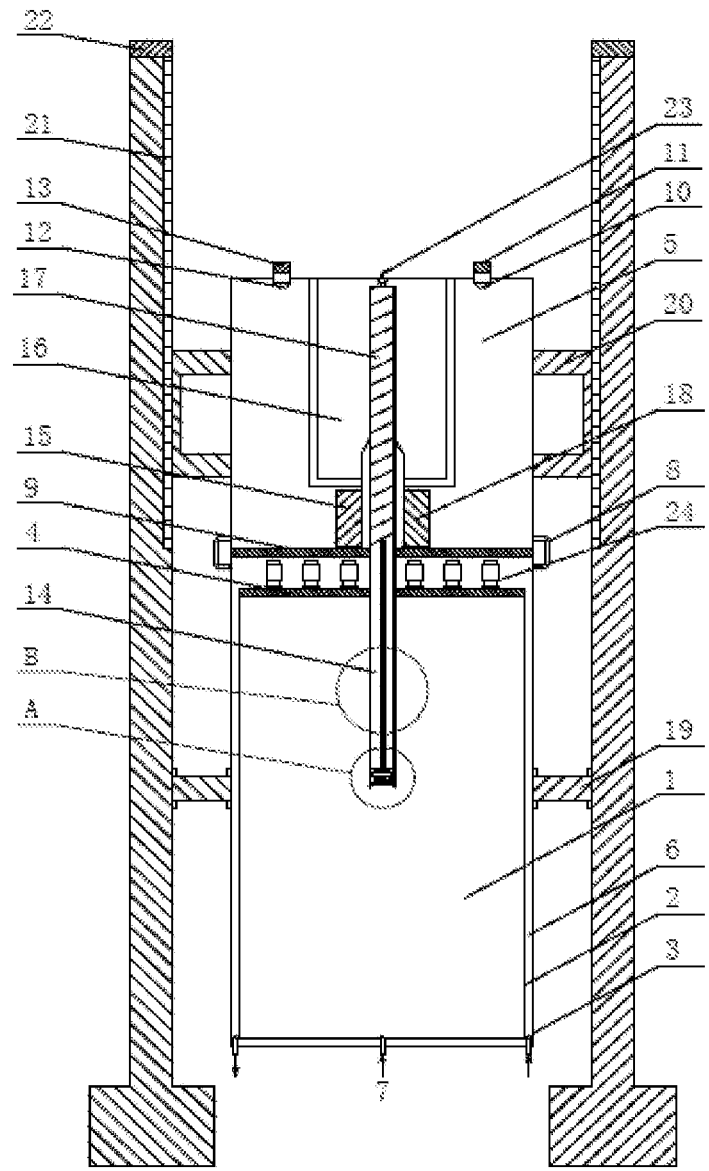
FIG. 1 is the overall structure diagram of the self drilling pressure simulation test device in the formation containing natural gas hydrate provided by the embodiment of the invention.
Figure 2:
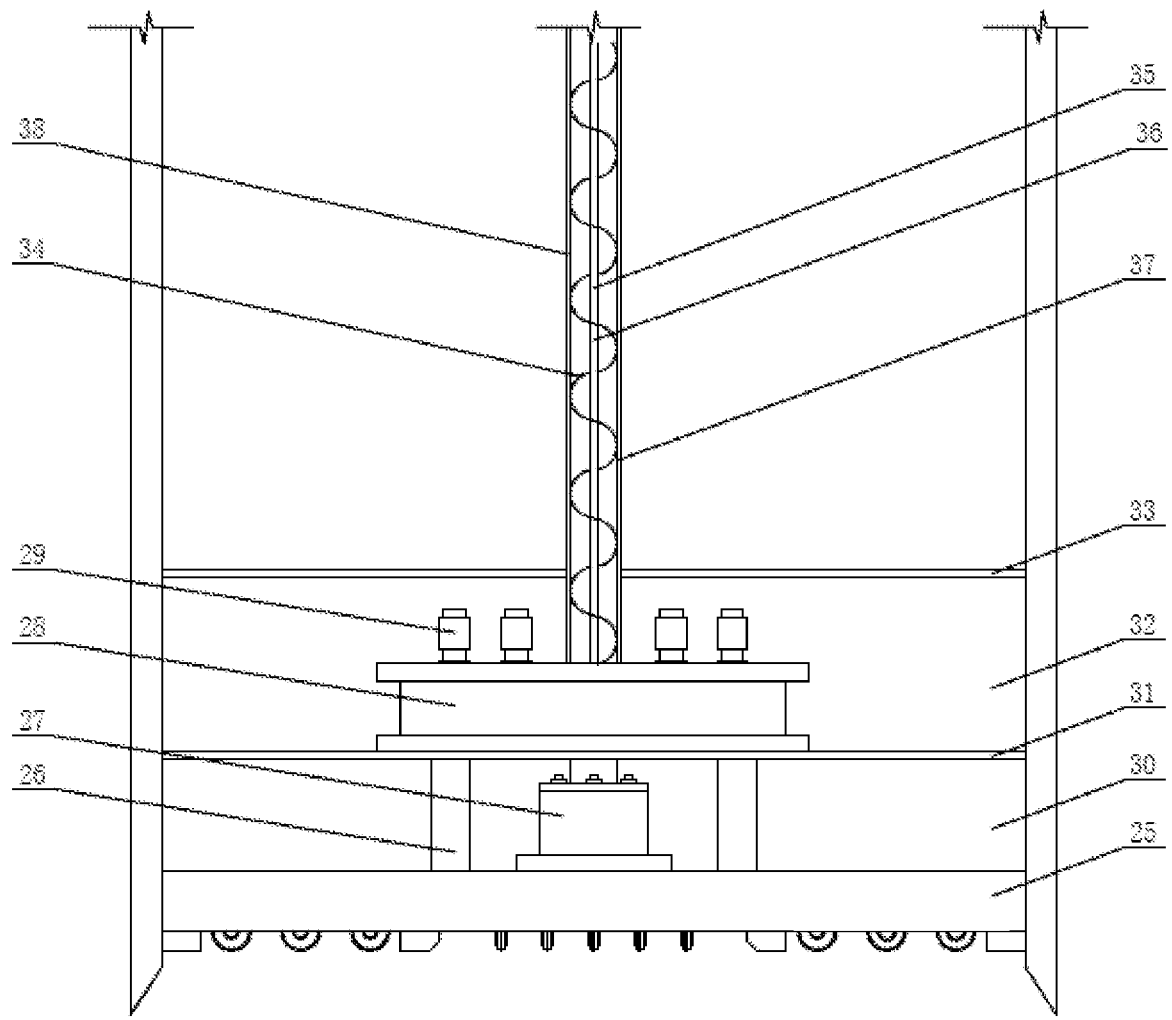
FIG. 2 is a partially enlarged structural diagram of part a in FIG. 1.
Figure 3:
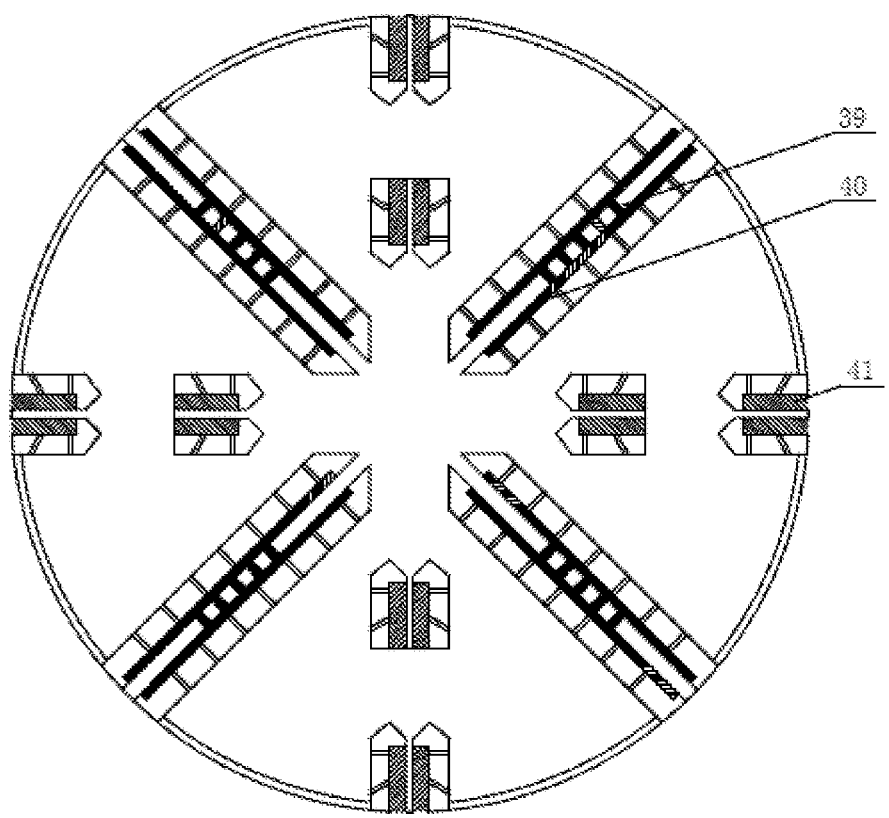
FIG. 3 is the structural diagram of the cutting cutter head applied in the self drilling side pressure simulation test device in the formation containing natural gas hydrate provided by the embodiment of the invention in one direction.
Figure 4:
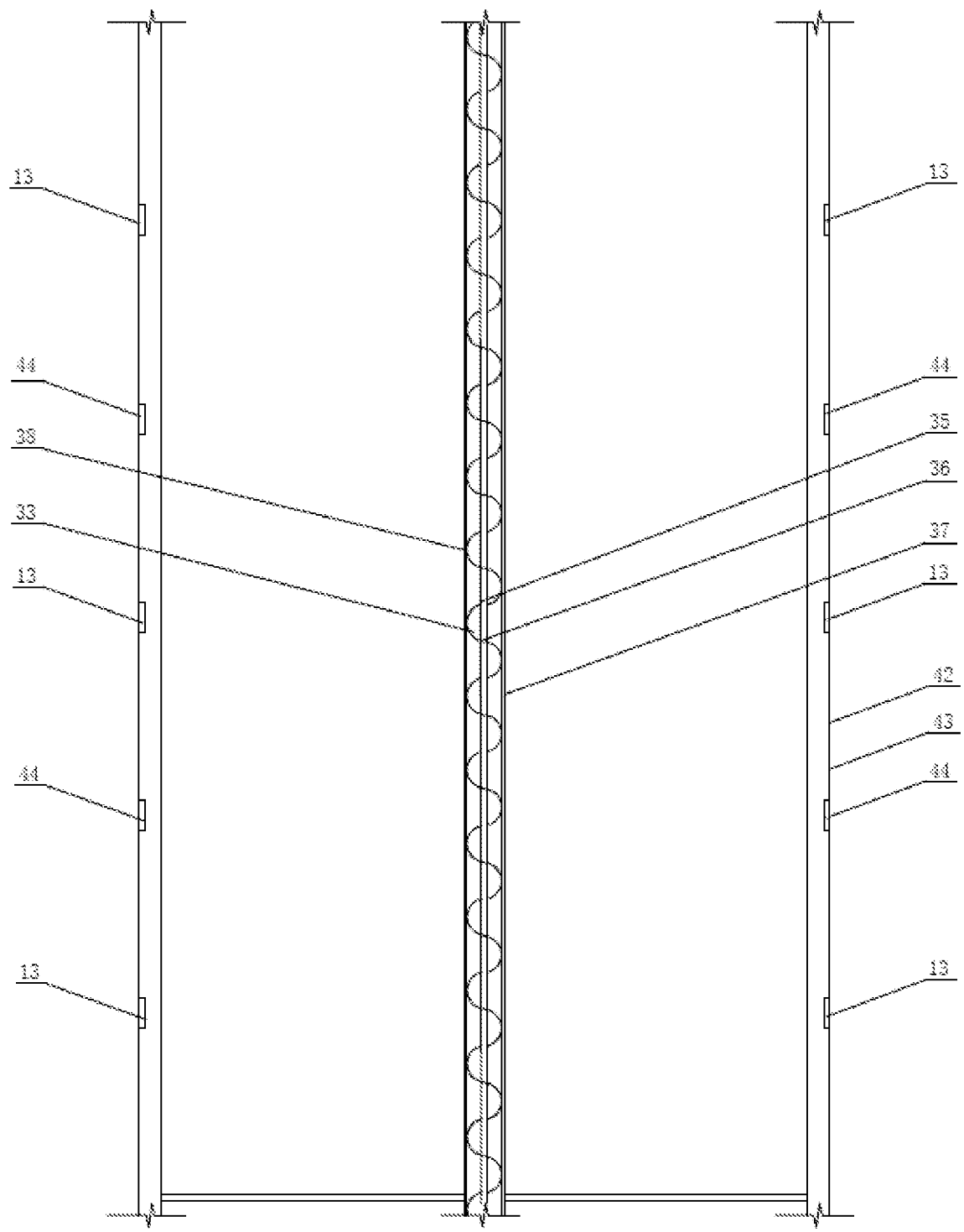
FIG. 4 is a partially enlarged structural diagram of Part B in FIG. 1.
Figure 5:
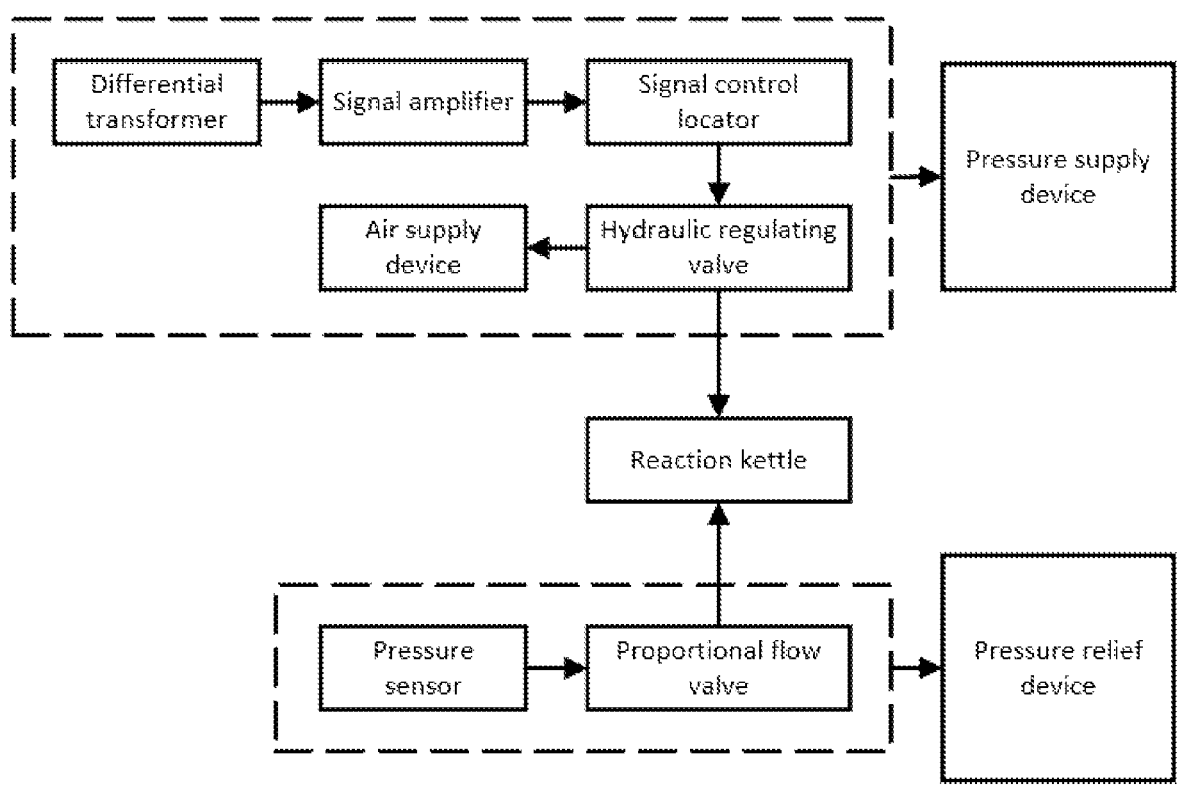
FIG. 5 is a schematic diagram of the signal flow direction relationship between components in the pressure control system applied in the self drilling side pressure simulation test device in the formation containing natural gas hydrate provided by the embodiment of the invention.

Referring to FIG. 1-FIG. 5, the self drilling side pressure simulation test device for formation containing natural gas hydrate proposed in the embodiment of the invention is mainly composed of seven parts: reactor subsystem, pressure control subsystem, temperature control subsystem, gas supply subsystem, self drilling side pressure test subsystem, height regulation subsystem, data acquisition and monitoring subsystem.

Among them, the reactor subsystem includes reactor 1, which includes reactor liner 2. Its design size is 700 mm high and 400 mm in diameter, which meets the requirements of three times the diameter of the drill bit. The material is titanium alloy to prevent the cracking and corrosion of reactor liner 2 under the condition of simulated natural gas. Methane passes through the temperature control subsystem. After reaching the set temperature (generally set to 3° C.), The reactor liner 2 is inflated through the air inlet and outlet 7, the reactor liner 2 is filled with saturated sediments, and the top of the reactor liner 2 is equipped with a reactor filter screen 4 to prevent the reactants from overflowing the reactor liner 2 during the experiment and ensure the accuracy of the measured mechanical parameters; The top of the reactor filter screen 4 is provided with a hydraulic jack 24 to simulate the overburden pressure of the formation containing natural gas hydrate; The outer wall of the reactor inner tank 2 is wound with a cooling pipe, the temperature control liquid in the cooling pipe is ethylene glycol, and the cooling pipe is a red copper pipe, which is locally welded with the outer wall of the reactor inner tank 2; An insulating layer 6 is arranged between the reactor inner tank 2 and the reactor shell 3, which plays the role of thermal insulation. The insulating layer 6 is made of rock wool with a thickness of 50 mm. The reactor shell 3 is made of stainless steel, which has the characteristics of corrosion resistance and protection of devices in the reactor. A sealing buckle 8 is set outside the reactor shell 3 and the reactor sealing cover 5 to play the role of mechanical sealing; An electromagnetic sealing gasket 9 is arranged between the reactor shell 3 and the reactor sealing cover 5. The power supply is connected at the beginning of the test. The electromagnetic sealing gasket 9 makes the reactor shell 3 closely connected with the reactor sealing cover 5 through electromagnetic induction, and the internal environment of the reactor is effectively isolated from the external environment. A differential transformer 11 is arranged on the top of the reactor sealing cover 5. The pressure in the reactor is measured through the LVDT linear variable differential pressure transformation system, and the hydraulic regulating valve 10 is controlled. The hydraulic regulating valve 10 is connected with the gas tank to deliver gas to the reactor and increase the pressure in the reactor; The pressure sensor 13 monitors the pressure in the reactor in real time. Once it exceeds the set value, it transmits a signal to the proportional flow valve 12, and the proportional flow valve 12 will stably discharge the pressure outside the reactor according to the set proportion to maintain the stability of the pressure in the reactor; The reactor sealing cover 5 is connected with the self drilling side pressure test subsystem to ensure the measurement accuracy of the test equipment; The reactor sealing cover 5 is provided with a temporary soil storage bin 16. The cut soil is transported to the temporary soil storage bin 16 through the screw conveyor 34. After the test, the temporary soil storage bin 16 can be unloaded and cleaned. The outside of the reactor shell 3 is connected with the turnover support 19 through high-strength bolts. The reactor shell is overturned to facilitate the cleaning of the reactor inner tank 3. The high-strength bolts are detachable to facilitate regular inspection and maintenance; The reactor sealing cover 5 is connected with the liftable support 20 through high-strength bolts. The liftable support can control the height of the reactor sealing cover 5 and automatically lock it after reaching the set height to increase the tightness of the reactor.

The pressure control subsystem includes a pressure boosting device and a pressure reducing device. The pressure boosting device includes a differential transformer 11 and a hydraulic regulating valve 10. The differential transformer 11 is an LVDT linear variable differential transformer, which has a linear relationship within a certain range. The differential transformer converts the pressure signal into an electrical signal, amplifies the electrical signal through the signal amplifier and transmits it to the signal control locator, Thus, the hydraulic regulating valve 10 is controlled; The hydraulic regulating valve 10 is a pcv5 hydraulic regulating valve, which is connected with the gas cylinder to stably increase the pressure in the reactor. The pressure reducing system includes a pressure sensor 13 and a proportional flow valve 12. The pressure sensor 13 monitors the pressure in the reactor in real time. Once the set value is exceeded, a signal is transmitted to the proportional flow valve 12, and the proportional flow valve 12 will stably discharge the pressure outside the reactor according to the set proportion to maintain the stability of the pressure in the reactor. In this embodiment, simulating the formation environment containing natural gas hydrate in reactor 1 mainly includes controlling the pressure in reactor 1 through hydraulic regulating valve 10, differential transformer 11, proportional flow valve 12 and pressure sensor 13 to simulate the deep-sea pressure environment; The overlying earth pressure above the natural gas hydrate formation is simulated by the hydraulic jack 24; Simulate the deep-sea temperature environment through the cooling pipe between the reactor tank 2 and the reactor shell 3; The gas is input through the gas inlet and outlet 7 to simulate the hydrate containing natural gas.

The temperature control subsystem includes cooling pipe, refrigerator and heat exchanger. The temperature control liquid passes through the refrigerator and heat exchanger. When the set temperature is reached, the temperature control liquid is circularly input to the cooling pipe to maintain the temperature of the inner tank of the reactor; The methane cylinder is connected with the refrigerator and heat exchanger. When the set temperature is reached, methane is injected into the inner tank 2 of the reactor through the gas inlet and outlet 7 to simulate the conditions containing natural gas hydrate.

The gas supply subsystem includes gas cylinder and methane cylinder. The gas cylinder is connected with hydraulic control valve 10 to increase the pressure in the reactor and simulate the deep-sea environment; The methane cylinder is first connected with the refrigerator and heat exchanger. After reaching the set temperature, it inflates the tank 2 of the reactor through the inlet and outlet 7 to simulate the conditions containing natural gas hydrate; The air supply subsystem is connected with the cable and impulse pipe inlet 23 to stably provide air source for the side pressure test device 14 in the test stage, so as to make the test data accurate and effective.

The self drilling side pressure test subsystem includes cutting device, measuring chamber and transmission device. The transmission device includes screw drive probe rod 17 and drilling motor 18 to control the rise and fall of the side pressure instrument. The cutting device includes cutting cutter head 25, mud storage bin 30, air pressure balance bin 32, bearing 27, hydraulic motor 29, screw conveyor 34 and screw conveying motor 15, In order to ensure that the surrounding soil is not disturbed, the measuring chamber includes pressure sensor 13, displacement sensor 44, elastic membrane 42 and protective armor 43, which are used to measure the physical parameters of the soil.

The height adjustment subsystem includes a turnover device and a lifting device. The turnover device includes a turnover support 19, which is connected with the reactor shell 3 through high-strength bolts. The reactor shell is overturned to facilitate the cleaning of the reactor inner tank 2. The high-strength bolts are detachable to facilitate regular inspection and maintenance; The base of the turnover support 19 is connected with the flat ground and can be fixed with the ground through expansion bolts to ensure the stability of the device. The reactor sealing cover 5 is connected with the liftable support 20 through high-strength bolts. The lifting motor 22 controls the vertical movement of the reactor sealing cover 5 by controlling the lifting transmission chain 21. At the end of the experiment, the reactor sealing cover 5 can be separated from the reactor shell 3 through the lifting transmission chain 21. At the beginning of the experiment, the height of the reactor sealing cover 5 can be reduced through the transmission chain 21, Automatically lock when the set value is reached to increase the tightness and stability of the reactor; The lifting bracket 20 is automatically locked after reaching the predetermined height, which can provide support reaction force for the side pressure tester when drilling in.

The data acquisition and monitoring subsystem includes pressure sensor, displacement sensor, temperature sensor, flow sensor and monitoring module. The pressure sensor 13 is located at the top of the reactor sealing cover 5 and the measurement chamber of the side pressure test device 14. The pressure sensor 13 at the top of the reactor sealing cover 5 is used to measure the pressure in the reactor, The pressure sensor located at the measuring chamber in the side pressure test device 14 includes pore water pressure sensor and lateral stress sensor, which are used to measure the engineering mechanical parameters of natural gas hydrate containing sediments; The displacement sensor 44 is located in the measurement cavity of the screw drive probe 17 and the side pressure test device 14, the displacement sensor located at the screw drive probe 17 is used to monitor the drilling depth and drilling rate of the side pressure test device 14, and the displacement sensor 44 located in the measurement cavity of the side pressure test device 14 is used to measure the displacement of the hole wall; The flow sensor is located at the inlet and outlet 7 and the inlet 23 of cable and impulse pipe, which is used to monitor and control the flow of inlet and outlet gas; The temperature sensor is located in the second part and bottom of the inner tank of the reactor, which is used to monitor the temperature in the reactor; The monitoring module is connected with the sensor to collect data and monitor the situation in the reactor and the side pressure test in real time.

Corresponding to the embodiment of the invention, the self drilling side pressure simulation test device for natural gas hydrate formation, which is used for indoor simulation test, comprises:

The self drilling side pressure tester includes a transmission device, a measuring chamber and a cutting device.

The transmission device includes a drilling motor 18 and a spiral drive probe rod 17. The drilling speed of the spiral drive probe rod 17 is controlled by the drilling motor 18. The transmission probe rod with spiral design can effectively control the drilling speed, which is generally set to 1 mm/s.

The side wall of the measuring chamber is provided with an elastic film 42, which is composed of two layers of 5 mm thick nitrile rubber film as a pressure vessel; The outside of the elastic film is provided with 18 strip-shaped protective armor 43 arranged equidistant along the circumferential direction to protect the elastic film; The elastic film 42 is provided with a pressure sensor 13 and a displacement sensor 44. The displacement sensor 44 is composed of a cantilever spring pasted with a resistance strain gauge and a lever type strain arm rotating with the shaft, which is evenly arranged along the axial direction. The cantilever spring is in contact with the elastic film 42 and can measure the radial displacement in multiple directions at the same time; The pressure sensor 13 includes a pore water pressure sensor and a lateral stress sensor. The pore water pressure sensor is close to the elastic membrane 42, three equally spaced pore water pressure sensors are set at the same height, the lateral stress sensor is installed in the elastic membrane, and three equally spaced lateral stress sensors are set at the same height, Each sensor is independently connected with the data acquisition and monitoring subsystem to avoid mutual interference and make the obtained data true and reliable.

The cutting device includes cutting equipment, driving equipment and transmission equipment. The cutting equipment includes positioning ring cutter and cutting cutter head 25. The positioning ring cutter is used to test the positioning of the device in the drilling process and prevent offset in the drilling process. The cutting cutter head 25 adopts panel type and can effectively balance with the excavation surface. The cutting tools used by the cutting cutter head 25 include main cutter 39, leading cutter 40 and scraper 41, The advance cutter 40 is used to pre loosen the soil and excavate the soil layer, the main cutter 39 is used to cut the soil, and the scraper 41 is used to shovel the soil into the warehouse; The cut soil is shoveled into the mud storage bin 30 through the scraper 41. In this embodiment, the cutting cutter head 25 is a planar structure, in which there is a hollow. The main cutter 39, the leading cutter 40 and the scraper 41 are arranged in the hollow of the cutting cutter head 25. The top of the mud storage bin 30 is provided with a mud storage bin partition 31 to prevent the cut soil from entering the measuring chamber and affecting the measurement accuracy of the instrument, The air pressure balance chamber 32 and the balance chamber diaphragm 33 act as a buffer chamber to balance the pressure of the measuring chamber and the cutting device, while maintaining the stability of the excavation surface. The driving equipment includes a hydraulic motor 29, which drives the rotation of the bearing 27 through the transmission bearing platform 28, the bearing 27 drives the rotation of the cutting cutter head 25 and the locating ring cutter, and the cutter head support frame 26 is located between the transmission bearing platform 28 and the cutting cutter head 25 to provide support reaction force for the cutter head in the process of cutting soil. The transmission equipment includes a screw center rod 35 and a screw conveyor 34. The screw conveyor 34 rotates around the screw center rod 35 to transport the soil in the sludge storage bin to the temporary soil storage bin 16 in the reactor sealing cover 5. The screw transmission motor 15 provides power for the screw conveyor 34 and controls its transmission speed; A multi-core cable 36 is arranged in the spiral center rod 35 to provide power for the cutting device; The outer wall of the screw conveyor is provided with a pressure guide pipe 38 and an infusion pipe 37, and a strain controller is arranged in the pressure guide pipe 38 to control the air pressure rate applied on the side pressure instrument. At the same time, it provides pressure for the air pressure balance chamber 32 to balance the excavation surface; The infusion pipe 37 provides lubricating fluid (generally distilled water) for the cutting device so that the cut soil can be smoothly discharged through the screw conveyor 34.

The self drilling side pressure simulation test device in the formation containing natural gas hydrate in the embodiment of the invention provides a method for using the indoor self drilling side pressure test simulation device, including:

The self drilling side pressure simulation test method proposed by the invention comprises a formation environment simulation stage containing natural gas sediments, a side pressure test device drilling stage, a side pressure test experiment and a data acquisition stage.

The simulation stage of formation environment containing natural gas sediments includes: after filling the tank with saturated water sediments, place the reactor filter screen 4 on the top of the sediment, and then lower the reactor sealing cover 5 to the preset height through the lifting support 20 to closely fit with the reactor; Open the hydraulic regulating valve 10 on the top of the sealing cover of the reactor and deliver gas to the device until the preset pressure is reached; The methane after passing through the temperature control subsystem is introduced into the tank of the reactor. At the same time, the hydraulic jack 24 on the filter screen of the reactor applies vertical pressure to the top of the sediment through the computer control system. When the pressure, temperature in the reactor and the vertical pressure at the top of the sediment reach the preset value stably, the experiment of the next stage can be carried out.

The drilling stage of the side pressure test device includes: after calibrating the elastic film binding force of the measurement chamber of the self drilling side pressure instrument and the comprehensive deformation of the instrument pipeline system after stress, install the side pressure test device in the simulation device; After reaching the preset formation environment containing natural gas hydrate, turn on the drilling motor 18, and the side pressure test device will drill down with the spiral drive probe rod 17; At the same time, the power supply of the hydraulic motor 29 is turned on, and the hydraulic motor drives the rotation of the cutting cutter head 25; The cut soil is transported to the temporary sludge storage bin 16 through the screw conveyor 35 and further cleaned after the test; During the drilling process of the pressure meter, distilled water shall be injected into the infusion pipe to ensure smooth drilling and improve the transmission efficiency of the cut soil; During drilling, an appropriate amount of gas can be injected through the impulse pipe to balance the pressure between the pressure meter and the surrounding environment.

The pressure side test and data acquisition stage includes: when the test device reaches the preset depth, remove the downward pressure of the drill pipe, stop the rotation of the hydraulic motor 29 and cut off the flushing water; The pressure value when the pressure in the test chamber reaches a stable value measured by the pressure sensor 13, which is the static side pressure of the soil; Open the pressure valve and officially start the test when the pressure of the pressure controller is balanced with the pressure in the measuring chamber; The elastic film wrapped on the outside of the measuring chamber expands under the action of the pressure in the chamber and compresses the surrounding soil at the same time. The data obtained by the displacement sensor, pore water pressure sensor and total stress sensor are transmitted, stored and post processed; When the measuring chamber reaches the predetermined expansion, stop the test at this stage.

Repeat the above steps, drill down and continue the side pressure test at the next depth. Before drilling, monitor the verticality of the test device through the displacement sensor on the bit. If necessary, correct the drilling angle through the positioning ring cutter until the side pressure test at all predetermined depths is completed.

Through the obtained test data, the self drilling pressure meter test can obtain the following results: determine the mechanical parameters such as foundation bearing capacity, soil shear modulus, pore water pressure, in-situ lateral pressure, static lateral stress coefficient, hole wall displacement and undrained shear strength, and analyze the shrinkage and expansion of cylindrical holes through the obtained loading curve.

Although preferred embodiments of the invention have been described, those skilled in the art may make additional changes and modifications to these embodiments once they know the basic inventive concept. Therefore, the appended claims are intended to be interpreted as including preferred embodiments and all changes and modifications falling within the scope of the present invention.

Obviously, those skilled in the art can make various changes and modifications to the invention without departing from the spirit and scope of the invention. Thus, if these modifications and variants of the invention fall within the scope of the claims of the invention and its equivalent technology, the invention is also intended to include these modifications and variants.

The invention claimed is:

1. A self drilling side pressure simulation test device for formation containing natural gas hydrate, which is characterized in that it comprises a reactor (1), a cutting tool, a mud conveying mechanism and a side pressure test device (14),
    the reactor (1) is used to fill the simulated substance of the formation containing natural gas hydrate to be tested,
    the cutting tool is arranged in the reactor (1), and the cutting tool can move up and down relative to the reactor (1),
    one end of the mud conveying mechanism is connected with the reactor (1) for outputting the mud cut by the cutting tool from the reactor (1);
    the side pressure test device (14) can complete the side pressure test experiment with the cutting tool moving to a set depth;
    the reactor (1) comprises a reactor inner tank (2), a reactor filter screen (4), a lifting rod (17);
    the filter screen (4) is arranged on the top of the reaction kettle (2);
    the lifting rod (17) can move up and down relative to the reactor filter screen (4);
    the cutting tool is fixedly connected to the bottom of the lifting rod (17);
    the mud conveying mechanism comprises a screw conveyor (34);
    the cutting tool comprises a cutting cutter head (25), a side wall and a mud storage bin diaphragm (31);
    the sludge storage bin (30) is enclosed between the cutting cutter head (25), the side wall and the sludge storage bin partition (31);
    the cutting tool (25) is provided with a hollow out;
    through the hollowing out, the mud cut by the cutting tool (25) can enter the mud storage bin (30);
    the screw conveyor (34) is communicated with the sludge storage bin (30) through one end thereof;
    the cutting tool further comprises a balance chamber diaphragm (33), a transmission bearing platform (28);
    the balance bin partition (33), the sludge bin partition (31) and the side wall are enclosed to obtain a pneumatic balance bin (32);
    the driving bearing platform (28) is pressed above the diaphragm (31) of the sludge storage bin;
    the reactor (1) further comprises a reactor shell (3) and a cooling pipe;
    a holding space is arranged between the inner tank (2) of the reactor and the shell (3) of the reactor;
    the cooling pipe is arranged in the holding space;
    the self drilling bypass pressure simulation test device for the formation containing natural gas hydrate also comprises an insulating layer (6);
    the insulating layer (6) is arranged in the holding space;
    the self drilling bypass pressure simulation test device for formation containing natural gas hydrate also comprises a reactor sealing cover (5);
    the reactor sealing cover (5) is arranged above the reactor inner tank (2), so that the reactor inner tank (2) forms a closed space;
    the self drilling side pressure simulation test device for formation containing natural gas hydrate also comprises a temporary soil storage bin (16), which is arranged in the sealing cover (5) of the reactor;
    the other end of the mud conveying mechanism is connected with the temporary soil storage bin (16);
    the self drilling bypass pressure simulation test device for the formation containing natural gas hydrate also comprises an electromagnetic sealing gasket (9);
    the electromagnetic sealing gasket (9) is arranged between the reactor sealing cover (5) and the reactor (1);
    the self drilling bypass pressure simulation test device for the formation containing natural gas hydrate also comprises a frame and a pair of turnover supports (19);
    the outer side of the turnover bracket (19) is arranged on the frame, the setting height of the pair of turnover brackets (19) is the same, and the turnover bracket (19) can rotate relative to the frame;
    the inner side of the turnover support (19) is fixedly connected to the reactor (1);
    the self drilling bypass pressure simulation test device for the formation containing natural gas hydrate also comprises a pair of liftable supports (20), a lifting transmission chain (21) and a lifting motor (22);
    the inner side of the liftable support (20) is fixedly connected to the reactor sealing cover (5);
    the outer side of the lifting support (20) is connected to the lifting transmission chain (21);
    the lifting motor (22) controls the lifting of the liftable support (20) by controlling the lifting transmission chain (21);
    the self drilling bypass pressure simulation test device for the formation containing natural gas hydrate further comprises a differential transformer (11), a signal amplifier, a signal control positioner, a hydraulic regulating valve (10), a proportional flow valve (12) and a pressure sensor (13);
    the hydraulic regulating valve (10) and the proportional flow valve (12) are arranged on the sealing cover (5) of the reactor, wherein the hydraulic regulating valve (10) is used to regulate the gas flow entering the reactor (1), and the proportional flow valve (12) is used to regulate the gas flow discharged from the reactor (1);
    the pressure sensor (13) is used to obtain the pressure data in the reactor (1);
    the differential transformer (11) is used to convert the pressure signal obtained from the pressure sensor into an electrical signal, amplify the electrical signal through the signal amplifier and transmit it to the signal control positioner, so as to control the opening of the hydraulic regulating valve (10).

2. The self drilling bypass pressure simulation test device for the formation containing natural gas hydrate according to claim 1, which is characterized in that the reactor (1) is provided with a gas inlet and outlet (7).

3. The self drilling bypass pressure simulation test device for the formation containing natural gas hydrate according to claim 1, which is characterized in that the simulated material for testing the formation containing natural gas hydrate includes saturated sediment and methane gas.

4. The self drilling bypass pressure simulation test device for formation containing natural gas hydrate according to claim 1, which is characterized in that it also comprises a drilling motor (18),
    the drilling motor (18) is used to control the movement of the spiral drive probe rod (17) in the vertical direction.

5. The self drilling bypass pressure simulation test device for formation containing natural gas hydrate according to claim 4, which is characterized in that it also comprises a measurement chamber, and the side wall of the measurement chamber is provided with an elastic film (42).

6. The self drilling side pressure simulation test device for formation containing natural gas hydrate according to claim 1, which is characterized in that it also comprises a main cutter (39), a leading cutter (40) and a scraper (41), The main cutter (39), the leading cutter (40) and the scraper (41) are arranged inside the cutting cutter head (25).

7. A self drilling bypass pressure simulation test method for gas hydrate containing formation, which is characterized in that the self drilling bypass pressure simulation test method for gas hydrate containing formation is realized based on the self drilling bypass pressure simulation test device for gas hydrate containing formation according to claim 1, the self drilling pressure meter simulation test method for the formation containing natural gas hydrate comprises the following steps:

filling the simulated substance of the formation containing natural gas hydrate to be tested into the reactor (1);

introducing methane with a set temperature into the reactor (1) to form a simulated test environment in the reactor (1);

causing the cutting tool to perform a cutting action on the simulated substance of the formation containing natural gas hydrate to be tested;

starting the mud conveying mechanism so that the cutting tool and the obtained mud are output from the reactor (1);

in the process of performing the cutting action of the simulated material of the natural gas hydrate containing formation to be tested, the side pressure test device (14) performs and completes the self drilling side pressure simulation test experiment of the natural gas hydrate containing formation.

8. The self drilling bypass pressure simulation test method for gas hydrate containing formation according to claim 7, which is characterized in that it further comprises the following steps, make the cutting tool perform the action of continuing drilling downward until the cutting tool reaches the next set depth, and complete the side pressure test experiment of the simulated substance of the formation containing natural gas hydrate to be tested at the next depth.

\* \* \* \* \*